United States Patent [19]
Dreessen et al.

[11] Patent Number: 5,464,446
[45] Date of Patent: Nov. 7, 1995

[54] BRAIN LEAD ANCHORING SYSTEM

[75] Inventors: Chrit Dreessen, Stein; Paul A. Gubbels, Brunsum; Paul Adams, M Geleen, all of Netherlands

[73] Assignee: Medtronic, Inc., Minneapolis, Minn.

[21] Appl. No.: 134,727

[22] Filed: Oct. 12, 1993

[51] Int. Cl.⁶ .................................................. A61N 1/05
[52] U.S. Cl. .................... 607/116; 607/139; 604/175
[58] Field of Search ............................ 128/642, 748; 607/116, 139; 604/175

[56] References Cited

U.S. PATENT DOCUMENTS

| | | | |
|---|---|---|---|
| 3,663,965 | 5/1972 | Lee, Jr. et al. | 604/175 X |
| 3,995,644 | 12/1976 | Parsons | 607/116 |
| 4,245,645 | 1/1981 | Arseneault et al. | 128/642 |
| 4,328,813 | 5/1982 | Ray | 128/791 |
| 4,350,159 | 9/1982 | Gouda | 128/303 |
| 5,004,457 | 4/1991 | Wyatt et al. | 604/158 |

FOREIGN PATENT DOCUMENTS

| | | | |
|---|---|---|---|
| 272356 | 11/1988 | Japan | 607/116 |
| 164373 | 6/1989 | Japan | 128/642 |

*Primary Examiner*—Lee S. Cohen
*Attorney, Agent, or Firm*—Michael J. Jaro; Harold R. Patton

[57] ABSTRACT

A system for anchoring a lead within a cranial burr hole. The system provides for a lead to be anchored in either of two sizes of burr holes. In further provides for the lead to remain secured to the stereotactic instrument during the installation of the lead anchoring system. The lead anchoring system consists of three parts: A plug having a central lead passage; a cap configured to fit over the plug while the lead is retained by the stereotactic instrument and thereby seal the burr hole and anchor the lead; and a socket designed to permit the plug to be fitted within a larger sized burr hole. In the preferred embodiment each of the parts, i.e. plug, socket and cap are constructed from silicone. The anchoring system of the present invention may be employed with a stimulation lead, a sensing lead, a combination thereof or any other elongated member requiring passage and fixation through the cranium.

25 Claims, 2 Drawing Sheets

BRAIN LEAD ANCHORING SYSTEM

FIELD OF THE INVENTION

This invention relates to an anchoring system and specifically to a system for anchoring a brain stimulation lead within a cranial burr hole.

BACKGROUND OF THE INVENTION

Electrical stimulation of the brain is under increasing use for such varied purposes as relief of chronic pain and treatment of movement disorders. A typical electrical brain stimulation system comprises a pulse generator operatively connected to the brain by a lead. The lead has an electrode at its distal end, designed to be implanted within the patient's brain, and a connector assembly at its proximal end, designed to connect to the pulse generator. Thus an electrical signal from the pulse generator is transmitted through the lead to the electrode and thus to the desired site in the patient's brain. Access to the desired position in the brain is generally accomplished by drilling a hole in the patient's skull or cranium.

Typically, a cranial drill (commonly referred to as a burr) is employed to provide access through the skull. Occasionally drilling through the skull may cause bleeding proximate to the hole. In such a situation a common technique is to redrill the hole in a larger diameter, thereby uncovering the bleeding vessel. Once uncovered the surgeon may treat the bleeding vessel.

Once a satisfactory burr hole has been achieve through the skull the desired stimulation site is located. Next the stimulation lead is placed with at least one electrode positioned at the desired stimulation site.

Typically the stimulation site is located and the lead electrode is positioned using a stereotactic instrument, such as that disclosed in U.S. Pat. No. 4,350,159 to Gouda, incorporated herein by reference. Use of such an instrument permits very precise movement within the brain, crucial to prevent unintended injury. Once the lead is positioned and tested to determine that the results of stimulation are satisfactory, it is critical that it not be moved. Even one millimeter of electrode travel may cause unsatisfactory results or even injury to the brain. As can be appreciated, traction on the portion of lead positioned outside the skull could easily cause movement of the portion positioned within the brain. Thus, reliable anchoring of the lead within the burr hole is necessary.

Previous designs of burr hole lead anchors required disconnecting the lead from the stereotactic instrument before the anchor could be positioned. For example, a burr hole lead anchoring system disclosed in U.S. Pat. No. 4,328,813 to Ray, incorporated herein by reference, consisted of an annular socket and cap to anchor a lead within a burr hole. Specifically the cap was positioned within the annular socket so the lead is trapped by the frictional fit between the socket and cap. This system, however had several drawbacks. First the lead was secured off center form the burr hole and thus could not be supported by the stereotaxic instrument during installation. Because the lead is unsupported while the anchor was installed, the lead was much more susceptible to dislodgement. Moreover the design of the plug and socket, in fact, have been found to cause dislodgement, specifically the lip of plug as it engages the socket tends to pull or dislodge lead. This design, moreover, does not have the ability to be fitted into various sized burr holes. As mentioned above, this can be a serious drawback, as a common technique to control bleeding within the skull, caused during the drilling of the burr hole, is to redrill the hole to a larger diameter and expose the ruptured vessel.

SUMMARY OF THE INVENTION

It is thus an object of the present invention to provide a simple and reliable system to anchor a lead within a cranial burr hole.

It is a further object of the present invention to provide a simple and reliable system to anchor a lead within a cranial burr hole which will permit the lead to be retained by a surgical instrument such as a stereotactic instrument while the anchoring system is being installed.

It is a still further object of the present invention to provide an anchoring system which permits a lead to be anchored within either of two sizes of burr hole.

These and other objects are met by the present invention which provides a simple and reliable system for anchoring a lead within a cranial burr hole. The system provides for a lead to be anchored in either of two sizes of burr holes. It further provides for the lead to remain secured to the stereotactic instrument during the installation of the lead anchoring system. The lead anchoring system consists of three parts: A plug having a central lead passage; a cap configured to fit over the plug while the lead is retained by the stereotactic instrument and thereby seal the burr hole and anchor the lead; and a socket designed to permit the plug to be fitted within a larger sized burr hole. In the preferred embodiment each of the parts, i.e. plug, socket and cap are constructed from silicone. The anchoring system of the present invention may be employed with a stimulation lead, a sensing lead, a combination thereof or any other elongated member requiring passage and fixation through the cranium.

DETAILED DESCRIPTION OF THE INVENTION

The present invention provides a simple and reliable system to anchor a lead within a cranial burr hole. For the purposes of this specification and claims, the term "lead" is used herein in its broadest sense and includes a stimulation lead, a sensing lead, a combination thereof or any other elongated member, such as the catheter, which may usefully be passed through a cranial burr hole.

The present invention provides a lead anchoring system to anchor a lead, connecting a pulse generator operatively to a brain, within a hole through a cranium or skull. The lead has an electrode located at its distal end, designed to be implanted within the patient's brain, and a connector assembly at its proximal end, designed to connect to an internal or external pulse generator by means of a dedicated extension cable. Thus an electrical signal from the pulse generator is transmitted through the lead to the electrode and therefore to the desired site in the patient's brain. Access to the desired position in the brain is generally accomplished by drilling a hole in the patient's skull or cranium.

Typically, a cranial drill (commonly referred to as a burr) is employed to provide access through the skull. Occasionally drilling through the skull may cause bleeding proximate to the hole. In such a situation a common technique is to redrill the hole in a larger diameter, thereby uncovering the bleeding vessel. Once uncovered the surgeon may treat it to control the bleeding. Once a satisfactory burr hole has been achieved the desired stimulation site is located. Next the stimulation lead is placed with at least one electrode positioned at the desired stimulation site. Typically the site is located and the lead electrode is positioned using a stereotactic instrument. Use of such an instrument permits very precise movement within the brain, crucial to prevent unintended injury. Once positioned and tested to determine whether stimulation is satisfactory, it is critical the electrode not move. Even one millimeter of electrode travel may cause unsatisfactory results or brain injury. As can be appreciated, traction on the external portion of lead could easily cause movement of the implanted electrode. Thus, reliable anchoring of the lead within the burr hole is necessary.

Figure 1:
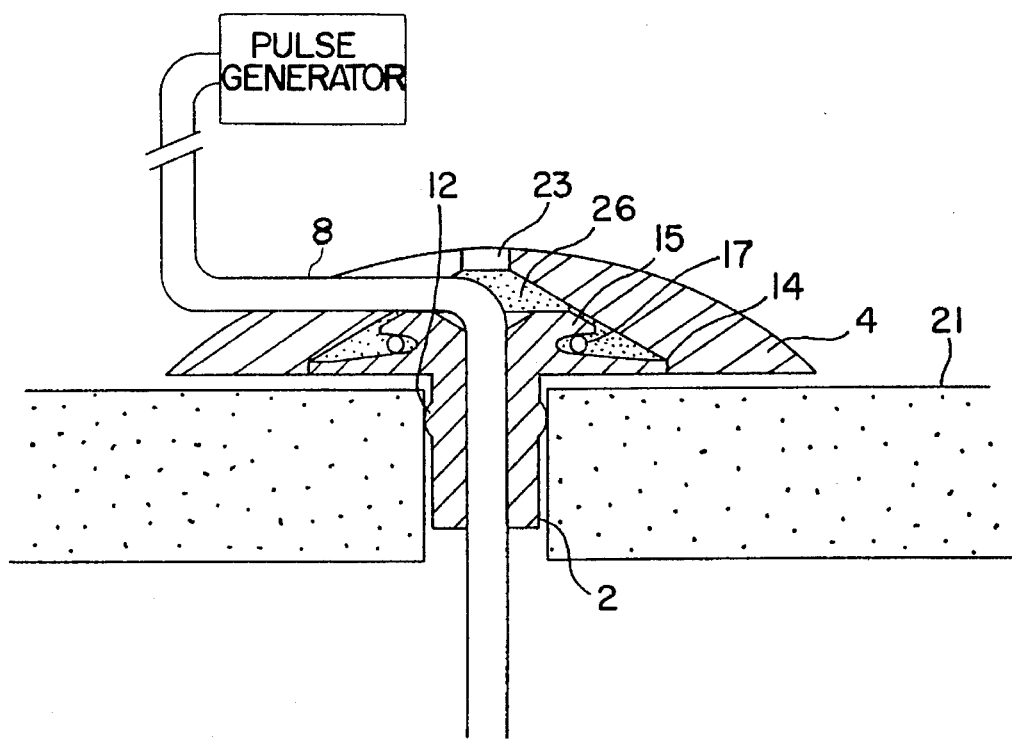
FIG. 1 is a cross sectional view of the lead anchoring system of the present invention placed in a first, relatively smaller, diameter burr hole.
Figure 2:
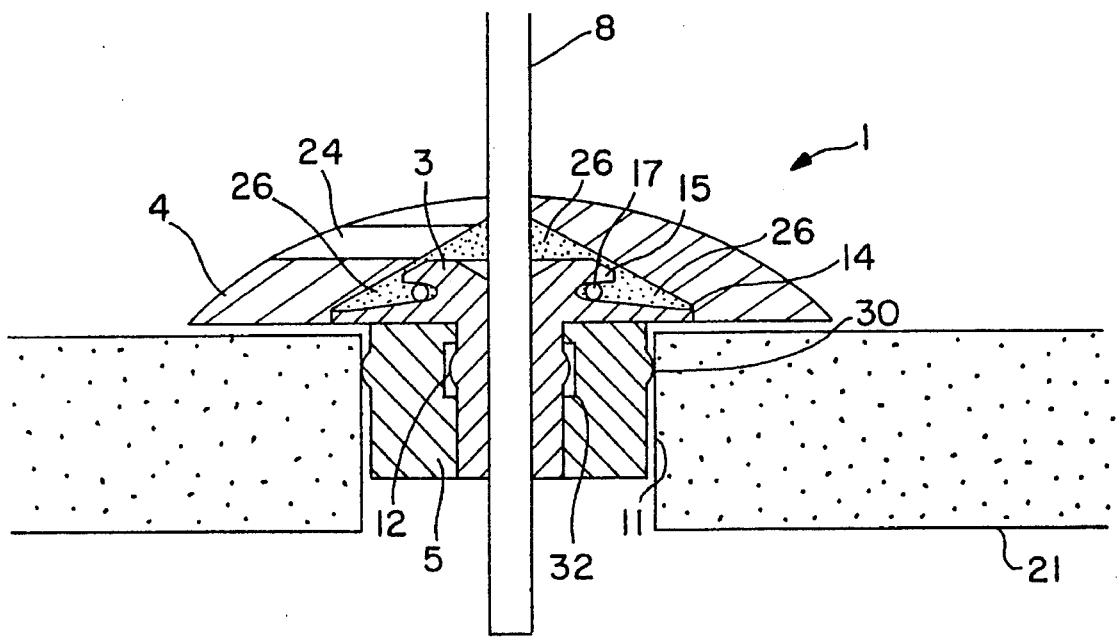
FIG. 2 is a cross sectional view of the lead anchoring system of the present invention placed in a second, relatively larger, diameter burr hole.

FIG. 1 is a cross sectional view of the lead anchoring system 1 of the present invention placed in a burr hole 2. As seen the anchoring system comprises a plug 3 and cap 4. As seen in FIG. 2 a socket 5 is also provided to be used along with plug 3 and cap 4 to anchor lead 8 in an enlarged diameter burr hole 11.

Figure 4:
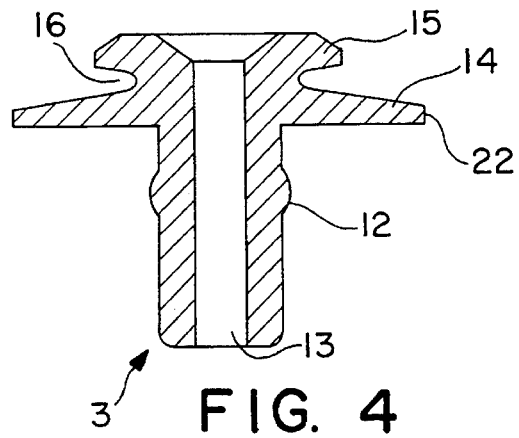
FIG. 4 is a cross sectional view of the plug used in the anchoring system of the present invention.

As seen in FIG. 4 plug 3 has a lead passage 13 centrally located. Rib 12 on plug 3 is configured to engage the inner surface of burr hole 2 and assist the fixation of plug within burr hole 2. A series of flanges 14, 15 are provided on upper surface of plug 3. Flanges 14, 15 define groove 16 used to retain suture 17. Suture 17 is wrapped around groove 16 to secure lead 8 in lead passage 13 of plug 3. In an alternative embodiment outer flange 14 may also provide a surface into which a fastener, such as a staple or suture (not shown) may be inserted to provide further fixation of plug into cranium. Outer flange 14, in addition, through its engagement of outer surface 22 with cap 4 helps to fix cap 4 to plug 3. Lead passage 13 in plug 3 is dimensioned to engage a lead (not shown) inserted therethrough.

Figure 6:
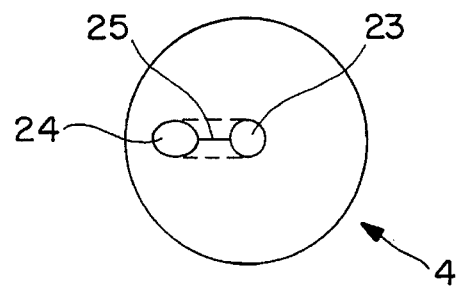
FIG. 6 is a top view of the cap used in the anchoring system of the present invention.

As seen lead passage 13 of plug 3 is coaxial with lead opening 23 in cap 4. Cap 4 further features off center opening 24 and slit 25, as best seen in FIG. 6. This configuration provides for the lead, once plug 3 and cap 4 are installed, to be removed from the positioning instrument (not shown) and then bent. In such a manner lead 8 is firmly anchored to the cap 4 and plug 3 and thus within the burr hole 2.

Figure 3:
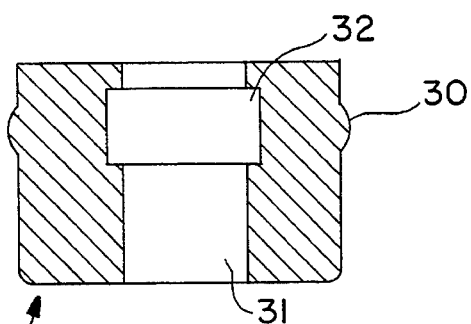
FIG. 3 is a cross sectional view of the socket used in the anchoring system of the present invention.
Figure 5:
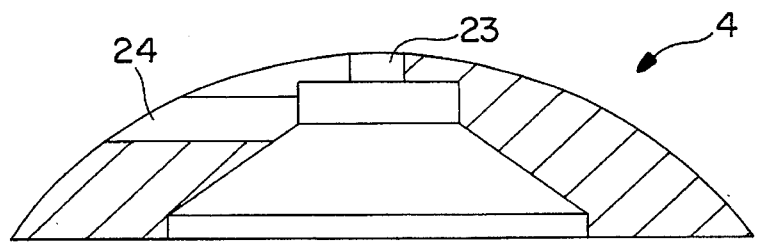
FIG. 5 is a cross sectional view of the cap used in the anchoring system of the present invention.

As seen in FIG. 2, when an enlarged diameter burr hole 11 is required, as in the case of a bleeding vessel, discussed above, socket 5 may be used as an adaptor to allow plug 3 to be anchored to cranium 21. Socket 5 has shoulder 30, best seen in FIG. 3, disposed to engage inner wall of enlarged diameter burr hole 11 and thereby fix socket 5 therein. Socket 5 may be sized in various diameters. Plug 3, on the other hand, is dimensioned to a fixed diameter. Thus an appropriately dimensioned socket 5 may be selected and used with plug 3 to thereby permit lead 8 to be anchored within any sized burr hole drilled.

Socket 5 further features plug lumen 31 therewithin and recess 32. Recess 32 cooperates with rib 12 on plug 3 to fix plug 3 within socket 5 and thus within cranium 21. Lead 8 is anchored in a similar fashion to the embodiment shown in FIG. 1.

Any suitable resilient biocompatible material may be used for plug 3, cap 4 and socket 5. In the preferred embodiment each component of the disclosed anchoring system is constructed from silicone.

Installation of the anchoring system of the present invention is as follows. Once a suitable burr hole 2 has been provided through cranium 21, cap 4 plug 3 and, if necessary to match an enlarged diameter burr hole 11, socket 5, are positioned along lead 8. Next, preferably through use of a stereotaxic instrument, now shown, lead 8 is suitably positioned within the brain. Once positioned, plug 3, or if socket is required socket 5, is moved along lead 8 and positioned within burr hole. If socket 5 was required to adapt plug 3 to an enlarged diameter burr hole 11, plug 3 is next moved along lead and installed within plug lumen 31. If socket 5 was not required plug 3 is next moved along lead 8 and positioned within burr hole 2. Once positioned lead 8 is fixed to plug 3, and specifically within lead passage 13 therethrough, by suture 17 tied about groove 16. Next cap 4 is positioned snugly to top of plug 3 through the engagement of outer flange 14 with cap 4, after medical adhesive 26 is applied.

Alternatively, installation of the anchoring system of the present invention may be accomplished as follows. Once a suitable burr hole 2 has been provided through cranium 21, cap 4 plug 3 and, if necessary to match an enlarged diameter burr hole 11, socket 5, are positioned within burr hole. Next, preferably through use of a stereotaxic instrument, not shown, lead 8 is suitable positioned through the anchoring system and burr hole to within the brain. Once positioned, lead 8 is fixed to plug 3, and specifically within lead passage 13 therethrough, by suture 17 tied about groove 16. Next cap 4 is positioned snugly to top of plug 3 through the engagement of outer flange 14 with cap 4, after medical adhesive 26 is applied.

Once cap 4 has been positioned, as previously discussed, lead 8 is firmly fixed within burr hole and may be disconnected from the stereotaxic instrument (not shown.) Because lead 8 remains mounted within the stereotaxic instrument during installation of the anchoring system 1, movement causing poor results or even injury is less likely to occur.

Once lead 8 is disconnected, it is folded through slit 25 and out off center opening 24, as depicted in FIG. 1. In such a manner lead 8 is securely anchored within burr hole.

Although the invention has been described in detail with particular reference to a preferred embodiment and alternate embodiments thereof, it will be understood variation and modifications can be effected within the scope of the following claims. Such modifications may include substituting elements or components which perform substantially the same function in substantially the same way to achieve substantially the same result for those described herein.

What is claimed is:

1. A system for anchoring a brain lead within a cranial burr hole comprising:

a socket having a central lumen, said socket having means for engaging a cranial burr hole to secure said socket to a cranium with said central lumen in general alignment with said burr hole;

a plug having means for fixing said plug within said central lumen, said plug further having means for fixing said plug within said cranial burr hole, said plug further having a lead lumen disposed therethrough, said lead lumen configured to engage a lead, said lead lumen configured to cooperate with said central lumen of said socket for mutual engagement of a lead within said central lumen, said plug further configured to close said central lumen, said plug having a first surface, said first surface having a flange, and a cap having a lumen designed to have a lead pass therethrough, said cap having means to engage with said flange of said plug.

2. The lead anchoring system of claim 1 wherein said means for engaging a cranial burr hole of said socket comprise a shoulder disposed on a surface of said socket to thereby engage a wall of said cranial burr hole.

3. The lead anchoring system of claim 1 wherein said means for engaging a cranial burr hole of said plug comprise a rib disposed on a surface of said plug to thereby engage a wall of said cranial burr hole.

4. The lead anchoring system of claim 2 wherein said shoulder is circumferentially disposed along said surface.

5. The lead anchoring system of claim 1 wherein means for fixing said plug within said central lumen comprises a rib disposed on a surface of said plug and a recess disposed on a surface of said socket to cooperate with said rib.

6. The lead anchoring system of claim 1 wherein means for fixing said plug within said central lumen are further configured to fix said plug within a differently sized cranial burr hole than said cranial burr hole.

7. The lead anchoring system of claim 4 wherein said system is constructed from a resilient material.

8. The lead anchoring system of claim 1 wherein said system is constructed from silicone.

9. A system for anchoring a brain stimulation lead within either a first size cranial burr hole or a second size cranial burr hole comprising:

a cylindrical socket corresponding to said first size cranial burr hole, said socket having means for engaging said first size cranial burr hole, said socket having a lumen corresponding to said second size cranial burr hole;

a plug corresponding to said second size cranial burr hole, said plug having means for engaging either an inner surface of said lumen of said socket or said second size cranial burr hole, said plug having a passage therethrough, said passage dimensioned to grasp a lead disposed therethrough; and a cap fitting over said plug, said cap having a first opening, said first opening dimensioned to permit a lead to pass therethrough.

10. The lead anchoring system of claim 9 wherein said means for engaging said first size cranial burr hole comprise a shoulder disposed on a surface of said socket to thereby engage a wall of said first size cranial burr hole.

11. The lead anchoring system of claim 10 wherein said shoulder is circumferentially disposed along said surface.

12. The lead anchoring system of claim 9 wherein said means for engaging said plug within said lumen of said socket comprises a rib disposed on a surface of said plug and a recess disposed on a surface of said socket to cooperate with said rib.

13. The lead anchoring system of claim 9 wherein said means for engaging said plug within said lumen of said socket are further configured to fix said plug within said first size cranial burr hole.

14. The lead anchoring system of claim 9 wherein said system is constructed from a resilient material.

15. The lead anchoring system of claim 14 wherein said material is silicone.

16. A brain stimulation system comprising:

an electrical pulse generator;

a lead having a proximal end and a distal end, said proximal end having a connector connecting said lead to said electrical pulse generator, said distal end having at least one electrode to connect said lead to said brain;

a lead anchor means for anchoring said lead within a first size cranial burr hole or a second size cranial burr hole, in a cranium said lead anchor means having a socket having means to fix said socket within said first size cranial burr hole, said socket having a lumen, a plug having means to fix said plug within said second size cranial burr hole, said plug further having means to fix said plug within said lumen of said socket, and a cap having a central lead passage, said cap having means for fixing said cap to said plug.

17. The brain stimulation system of claim 16 wherein said means to fix said socket within said first size cranial burr hole comprises a shoulder positioned along a surface of said socket.

18. The brain stimulation system of claim 16 wherein said means to fix said plug within said second size cranial burr hole comprises a rib positioned along a surface of said plug.

19. The brain stimulation system of claim 16 wherein said means to fix said plug within said second size cranial burr hole comprises a flange on a surface of said plug, said flange providing a site to install at least one fastener through said plug into said cranium.

20. The brain stimulation system of claim 16 wherein said means to fix said plug within said lumen of said socket comprises a recess within an inner surface of said socket and a rib positioned on said plug to cooperatively engage said recess to thereby fix said plug therewithin.

21. The brain stimulation system of claim 16 wherein said means for fixing said cap to said plug comprises a flange on said plug.

22. A system for anchoring a brain lead within a cranial burr hole comprising:

a plug having means for fixing said plug within a cranial burr hole, said plug further having a lead lumen disposed centrally therethrough, said plug further having a suture groove about said lead lumen, said lead lumen configured to engage a lead, said lead lumen configured to cooperate with a suture disposed about said suture groove and engage a lead within said lead lumen; and a cap having a lumen designed to have a lead pass therethrough, said cap engaging with said plug.

23. The lead anchoring system of claim 22 further comprising a socket having a central lumen, said socket having means for engaging a cranial burr hole to secure said socket to a cranium with said central lumen in general alignment with said burr hole, said plug having means for fixing said plug within said central lumen of said socket.

24. The lead anchoring system of claim 23 wherein said means for fixing said plug within said central lumen of said socket comprise a shoulder disposed on a surface of said plug to thereby engage said socket burr hole.

25. The lead anchoring system of claim 22 wherein said means for engaging a cranial burr hole of said plug comprise a rib disposed on a surface of said plug to thereby engage a wall of said cranial burr hole.

\* \* \* \* \*